US00PP33175P2

(12) United States Plant Patent
Olesen

(10) Patent No.: US PP33,175 P2
(45) Date of Patent: Jun. 22, 2021

(54) COMPACT FLORIBUNDA ROSE PLANT NAMED 'POULCAS062'

(50) Latin Name: *Rosa hybrida*
Varietal Denomination: Poulcas062

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 16/873,998

(22) Filed: Sep. 3, 2020

(51) Int. Cl.
*A01H 5/02* (2018.01)
*A01H 6/74* (2018.01)

(52) U.S. Cl.
USPC ..... Plt./141
CPC ..... *A01H 6/749* (2018.05)

(58) Field of Classification Search
USPC ..... Plt./141
CPC ..... A01H 6/749; A01H 5/02
See application file for complete search history.

*Primary Examiner* — Keith O. Robinson

(57) ABSTRACT

A new garden rose plant of the Compact Floribunda class which has abundant, red-purple flowers and attractive foliage. This new and distinct variety has shown to be uniform and stable in the resulting generations from asexual propagation.

2 Drawing Sheets

Botanical designation: *Rosa hybrida.*
Variety denomination: 'Poulcas062'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulcas062', originated as a single seedling from the stated cross.

The new variety may be distinguished from its male pollen parent and female seed parent primarily by the following characteristics. The male pollen parent plant has near white flowers while the new variety has red-purple flowers. The female seed parent plant has pink flowers while the new variety has red-purple flowers.

The objective of the hybridization of this rose variety was to create a new and distinct variety with unique qualities, such as:

1. Uniform and abundant red-purple flowers;
2. Vigorous, but compact growth when propagated on its own roots;
3. Exceptional disease resistance.

This combination of qualities is not present in previously available commercial cultivars of this type, known to the inventor, and distinguish 'Poulcas062' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulcas062' was selected in the spring of 2011 by the inventor as a single plant from the progeny of the aforementioned hybridization.

Asexual reproduction of 'Poulcas062' by rooted cuttings was first done by Mogens N. Olesen in the nursery in Fredensborg, Denmark in July, 2011. This initial and other subsequent asexual propagations conducted in controlled environments have demonstrated that the characteristics of 'Poulcas062' are true to type and are transmitted from one generation to the next.

DESCRIPTION OF THE DRAWING

The accompanying color illustrations show as true as is reasonably possible to obtain in color photographs of this typo, the typical characteristics of the buds, flowers, leaves, and stems, of 'Poulcas062'.

Specifically illustrated in FIG. 1 of the drawings is a cluster of open flowers on the branch, open flowers, petals and sepals detached showing reproductive flower parts and receptacle.

Figure 1:
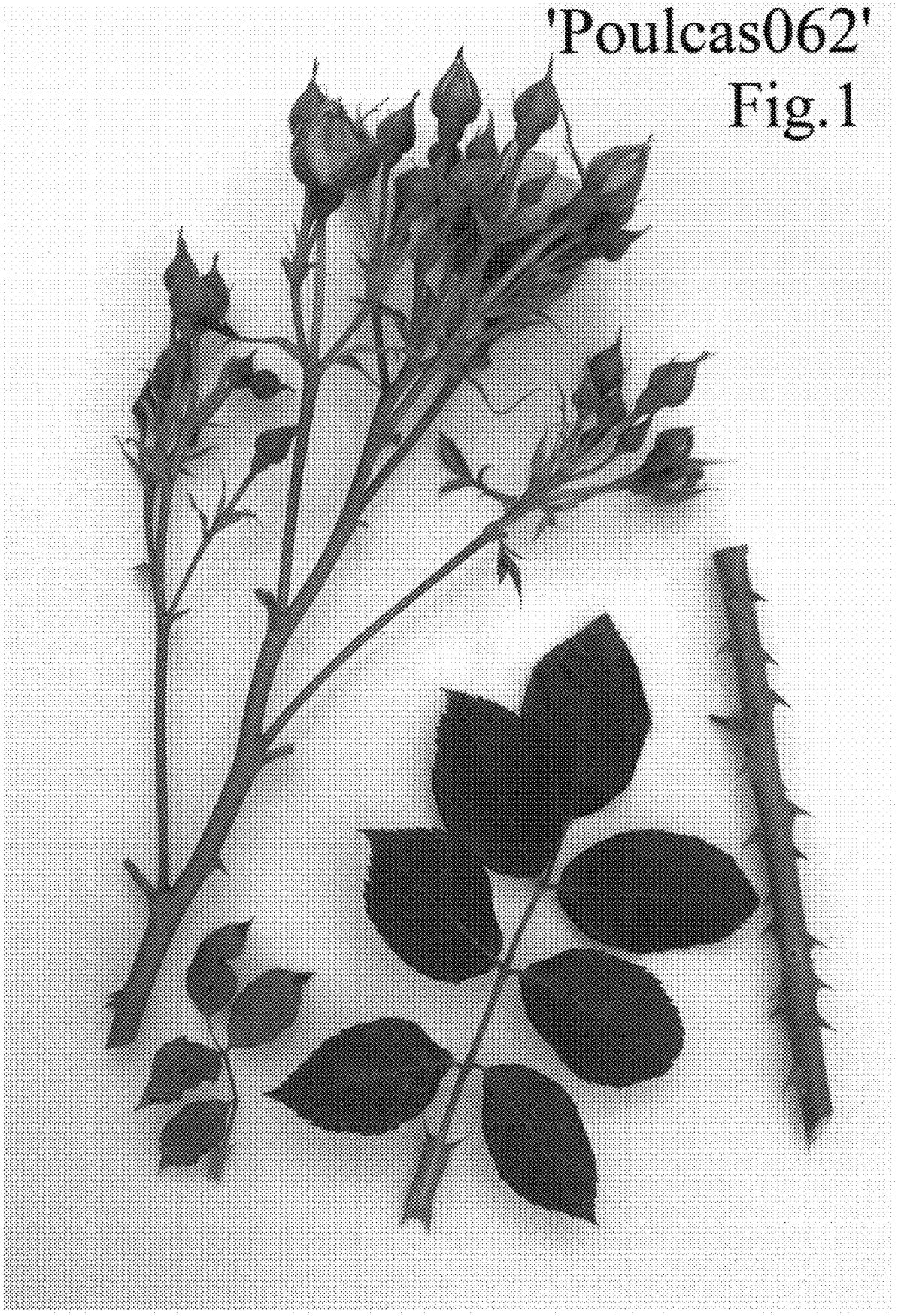
Figure 2:
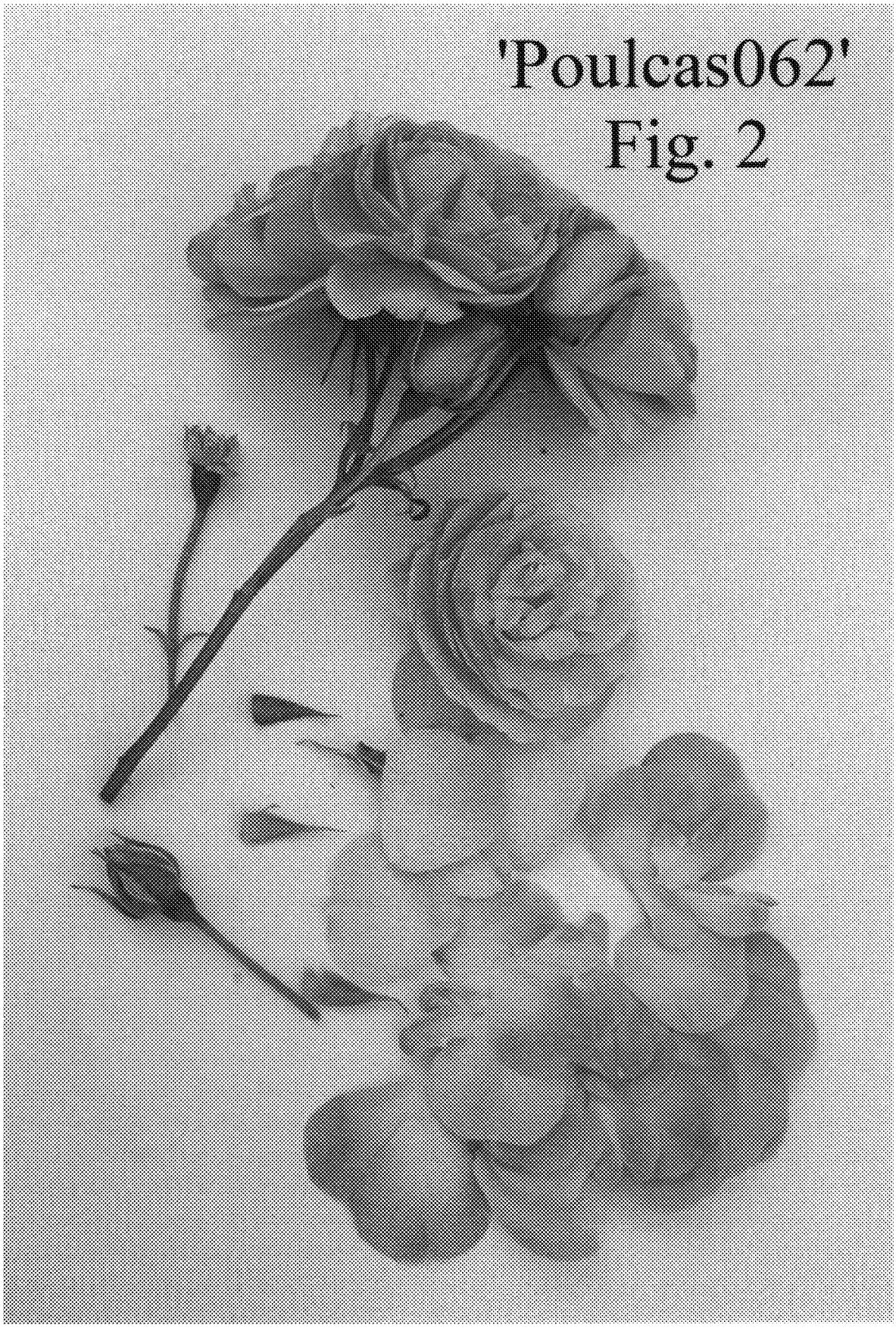

Specifically illustrated in FIG. 2 of the drawings are a flowering branch with flower buds showing arrangement of clusters on peduncles, bare stem, and leaves. Plants shown are 2 years of age.

DETAILED DESCRIPTION OF THE VARIETY

The following is a description of 'Poulcas062', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas54', are compared to 'Poulcas062' in Chart 1.

CHART 1

| | 'Poulcas062' | 'Pou1cas54' |
|---|---|---|
| Petal Count | 45 | 30 |
| Flower Diameter | 75 mm | 95 mm |

CHART 1-continued

| | 'Poulcas062' | 'Pou1cas54' |
|---|---|---|
| General Tonality of Flower Color | Red-Purple Group 65A and 65B | Red-Purple Group 68B |

FLOWER AND FLOWER BUD

Blooming habit: Continuous.

Flower bud:

*Size*.—Upon opening, 25 mm in length from base of receptacle to end of bud. Bud diameter is 11 mm.

*Bud form*.—Ovoid.

*Bud color*.—As sepals divide petals are Red Group 51B and Yellow Group 12D.

*Sepal inner surface*.—Color: Yellow-Green Group 146D. Surface: Lightly pubescent.

*Sepal outer surface*.—Color: Yellow-Green Group 144A with intonations of Greyed-Red Group 181A. Texture: Smooth, with many stipitate glands at margins

*Sepal shape*.—Apex: Cirrhose. Base: Flat at union with receptacle.

*Sepal margin*.—Margins have moderate foliaceous appendages on three of the five sepals.

*Sepal size*.—21 mm long, 10 mm wide.

*Receptacle*.—Texture: Smooth. Size: 7 mm in height, 6 mm wide. Color: Yellow-Green Group 144A with intonations of Greyed-Red Group 182A. Shape: Campanulate.

*Pedicel*.—Surface: Smooth. Length: About 26 mm. Diameter: 3 mm on average. Color: Yellow-Green Group N144A with intonations of Greyed-Red Group 182B. Strength: Strong.

*Peduncle*.—Length: 2 to 10 cm. Diameter: About 4 mm. Color: Yellow-Green Group N144A with intonations of Greyed-Red Group 182B. Texture: Smooth.

Flower bud development: Flower buds are borne in clusters of 3 to 9 flower buds per stem. Development as a panicle.

Flower bloom:

*Fragrance*.—Moderate rose scent.

*Duration*.—The blooms have a duration on the plant of approximately 14 days. Petals fall cleanly away from plant after flowers have fully matured.

*Size*.—Flower diameter is 75 mm when open. Flower depth is 30 mm.

*Flower shape*.—Open cup, double flower, with petals that curve out from the center.

*Shape of flower, side view*.—The upper portion is flat convex. The lower portion is flat concave.

Petalage: Under normal conditions, flowers have about 45 petals.

General tonality of flower: Open flowers are Red-Purple Group 65A and 65B.

Petal color:

*Upon opening, outer & inner petals*.—Upper surface: Red-Purple Group 62A. At the basal zone Red-Purple Group 65B. Lower surface: Red-Purple Group 56B at the basal zone Red-Purple Group 65A towards margins. Other intonations of Yellow-White Group 158D at the petal base, point of attachment.

*Basal petal spots, upon opening*.—Upper surface: Yellow-Green Group 150D. Lower surface: Yellow-Green Group 150D.

*After opening, outer petals*.—Upper surface: Red-Purple Group 69D with streaks of Red-Purple Group 70C. Lower surface: Red-Purple Group 69B shaded with Red-Purple Group 65B.

*After opening, inner petals*.—Upper surface: Red-Purple Group 69D with streaks of Red-Purple Group 70C. Lower surface: Red-Purple Group 69B shaded with Red-Purple Group 65B.

*Basal petal spots, after opening*.—Upper surface: Green-White Group 157D. Lower surface: Green-White Group 157D.

Petals:

*Petal reflex*.—Somewhat reflexed.

*Margin*.—Entire and uniform. Moderate undulations.

*Shape*.—Broad and elliptic. Apex shape: Rounded. Base shape: Acute.

*Size*.—35 mm (l)×33 mm (w).

*Texture*.—Smooth.

*Thickness*.—Average.

Petaloids:

*Size*.—15 mm (l) by 10 mm (w).

*Quantity*.—About 12.

*Shape*.—Elliptical with an acute base and rounded apex.

*Color*.—Red-Purple Group 73C above and underneath. Petaloid spot Yellow-Green Group 150D.

Reproductive flower parts:

*Pollen*.—None observed.

*Anthers*.—Size: 2 mm in length. Color: Greyed-Orange Group 163B. Quantity: 30 on average.

*Filaments*.—Color: Yellow Group 4A. Length: 7 mm.

*Pistils*.—Length: 3 mm. Quantity: 25 on average.

*Stigmas*.—Color: Greyed-Yellow Group 160D.

*Styles*.—Color: Greyed-Yellow Group 160D.

*Location of stigmas*.—Inferior in location relative to the length of the filaments and the height of the anthers.

*Hips*.—None Observed.

PLANT

Plant growth: Upright, well branched, and bushy. Plants are 75 cm in height, and 75 cm wide.

Stems:

*Color of juvenile growth*.—Yellow-Green Group 144B.

*Color of mature growth*.—Yellow-Green Group 144B.

*Length*.—Canes are about 35 cm from the base of the plant to the flowering portion.

*Diameter*.—About 10 mm.

*Internodes*.—On mature canes about 50 mm between nodes.

*Surface texture*.—Young wood: Smooth. Older wood: Smooth.

Long prickles:

*Incidence*.—12 prickles per 10 cm of stem.

*Size*.—Average length of prickles on mature stems is 6 mm.

*Shape*.—Upper portion is linear. Lower portion is concave.

*Color*.—Juvenile prickles: Greyed-Orange Group 164C and Greyed-Red Group 180D. Mature prickles: Greyed-Orange Group 164C and Greyed-Red Group 180D.

Plant foliage:

*Compound leaf*.—155 mm (l)×135 (w).

*Quantity*.—2 leaves per 10 cm of stem on average.

*Leaf bearing angle to the stem*.—45 degrees.

*Color of juvenile foliage*.—Upper side: Yellow-Green Group 144A with intonations of Greyed-Red Group 179A at the margins. Lower side: Yellow-Green Group 144B.

*Color of mature foliage*.—Upper side: Yellow-Green Group 146B. Lower side: Yellow-Green Group 146C.

Plant leaves and leaflets:

*Stipules*.—Size: 13 mm long, 7 mm wide. Quantity: 2 per compound leaf. Shape: Linear, slightly broad based with outward extending apices. Margins: Finely serrated. Color: Yellow-Green Group 144A.

*Petiole*.—Length: About 35 mm. Diameter: 2 mm. Upper surface color: Yellow-Green Group 144A. Lower surface color: Yellow-Green Group 144A.

*Rachis*.—Length: About 56 mm. Upper surface color: Yellow-Green Group 144A. Lower surface color: Yellow-Green Group 144A.

*Leaflet*.—Quantity: Normally 7 leaflets. Margins: Serrated. Size: Terminal leaflets are about 65 mm long, 45 mm wide. Shape: Generally elliptical. Base: Rounded. Apex: Acute. Texture: Smooth. Thickness: Average. Arrangement: Odd pinnate. Venation: Reticulate. Glossiness; Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulcas062', substantially as illustrated and described herein, due to its abundant red-purple flowers, disease resistance, and extended period of bloom.

* * * * *

'Poulcas062'

'Poulcas062'